United States Patent
Sutton et al.

(10) Patent No.: US 10,891,778 B2
(45) Date of Patent: Jan. 12, 2021

(54) APPARATUS AND METHOD FOR PRODUCING THREE-DIMENSIONAL MODELS FROM MAGNETIC RESONANCE IMAGING

(71) Applicant: THE BOARD OF TRUSTEES OF THE UNIVERSITY OF ILLINOIS, Urbana, IL (US)

(72) Inventors: Bradley P. Sutton, Savoy, IL (US); Xi Peng, Urbana, IL (US); Matthew Bramlet, Peoria, IL (US); Kevin Urbain, Peoria, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 80 days.

(21) Appl. No.: 16/243,872

(22) Filed: Jan. 9, 2019

(65) Prior Publication Data
US 2019/0213779 A1   Jul. 11, 2019

Related U.S. Application Data

(60) Provisional application No. 62/615,464, filed on Jan. 10, 2018.

(51) Int. Cl.
*G06K 9/00*    (2006.01)
*G06T 15/08*   (2011.01)
(Continued)

(52) U.S. Cl.
CPC .............. *G06T 15/08* (2013.01); *A61B 5/055* (2013.01); *A61B 5/7267* (2013.01); *G06T 7/11* (2017.01);
(Continued)

(58) Field of Classification Search
CPC combination set(s) only.
See application file for complete search history.

(56) References Cited

U.S. PATENT DOCUMENTS

| 9,968,257 B1 * | 5/2018 | Burt ..................... A61B 5/7267 |
| 2008/0075343 A1 * | 3/2008 | John ..................... A61B 6/541 |
| | | 382/131 |
| 2016/0328630 A1 | 11/2016 | Han et al. |

FOREIGN PATENT DOCUMENTS

WO    2017074890 A1    5/2017

OTHER PUBLICATIONS

Zreik, "Deep learning analysis of the myocardium in coronary CT angiography for identification of patients with functionally significant coronary artery stenosis," Nov. 2017, Elsevier (Year: 2017).*

(Continued)

*Primary Examiner* — Alex Kok S Liew
(74) *Attorney, Agent, or Firm* — Guntin & Gust, PLC; Matthew Tropper

(57) ABSTRACT

Aspects of the subject disclosure may include, for example, a method comprising: receiving, by a processing system including a processor, an input three-dimensional dataset comprising a first plurality of two-dimensional images of all or a portion of a subject; applying, by the processing system, bias field correction to the input three-dimensional dataset to generate a corrected three-dimensional dataset comprising a second plurality of two-dimensional images; and generating, by the processing system, a labeled three-dimensional dataset comprising a third plurality of two-dimensional images, wherein the labeled three-dimensional dataset further comprises one or more labels indicating an anatomical structure, and wherein the labeled three-dimensional dataset is generated via a convolutional neural network based upon the corrected three-dimensional dataset and based upon a pre- (Continued)

viously trained three-dimensional dataset. Additional embodiments are disclosed.

20 Claims, 11 Drawing Sheets

(51) Int. Cl.
  *G06T 7/11*     (2017.01)
  *A61B 5/055*    (2006.01)
  *A61B 5/00*     (2006.01)
  *G06T 19/00*    (2011.01)

(52) U.S. Cl.
  CPC ........ *G06T 19/00* (2013.01); *A61B 2576/023* (2013.01); *G06T 2207/10088* (2013.01); *G06T 2207/20081* (2013.01); *G06T 2207/20084* (2013.01); *G06T 2207/20132* (2013.01); *G06T 2210/41* (2013.01); *G06T 2219/004* (2013.01)

(56) References Cited

OTHER PUBLICATIONS

Press releases from "Materialise" https://www.materialise.com/en/press-releases, Accessed Jan. 9, 2019, 3 pages.
"About Materialise", https://www.materialise.com/en/about-materialise, Accessed Jan. 9, 2019, 2 pages.
"FAST—FslWili", https://fsl.fmrib.ox.ac.uk/fsl/fslwiki/FAST, Jan. 13, 2016.
Cicek, Ozgun et al., "3D U-Net: Learning Dense Volumetric Segmentation from Sparse Annotation", arXiv:1606.06650 [cs.CV]., 8 pages.
Coates, Adam et al., "An Analysis of Single-Layer Networks in Unsupervised Feature Learning", Proc. 14th Intl Conf on Artificial Intelligence and Statistics (AISTATS), 2011, 9 pages.
Dou, Qi et al., "3d deeply super-vised network for automatic liver segmentation from ct volumes", arXiv preprint arXiv:1607.00582, 2016, 8 pages.
Hoffman, Julien I. et al., "The incidence of congenital heart disease", J Am Coll Cardiol. 39(12), 2002, 11 pages.
Jia, Yangqing et al., "Caffe: Convolutional Architecture for Fast Feature Embedding", Proceedings of the 22nd ACM international conference on Multimedia, 2014, 4 pages.
Krizhevsky, Alex et al., "ImageNet Classification with Deep Convolutional Neural Networks", Adv Neural Inf Process Syst 2012:1097-1105, 2012, Abstract.
Lecun, Yann et al., "Convolutional Networks and Applications in Vision", IEEE International Symposium on Circuits and Systems (ISCAS), 2010, 4 pages.
Li, Chunming et al., "Multiplicative intrinsic component optimization (MICO) for MRI bias field estimation and tissue segmentation", Magnetic Resonance Imaging 32 (2014) 913-923, 2014, 11 pages.
McGaghie, William C. et al., "A critical review of simulation-based medical education research: 2003-2009. Med Educ. Wiley Online Library", 20078756, 2010, 14 pages.
Merkow, Jameson et al., "Dense volume-to-volume vascular boundary detection", arXiv preprint arXiv:1605.08401, 2016, 8 pages.
Pace, Danielle F. et al., "Interactive whole-heart segmentation in congenital heart disease", International Conference on Medical Image Computing and Computer-Assisted Intervention, 2015, 9 pages.
Peng, Xi et al., IEEE Transaction on Biomedical Engineering, vol. 14, No. 8, Feb. 2018, 4 pages.
Peters, Jochen et al., "Automatic whole heart segmentation in static magnetic resonance image volumes", International Conference on Medical Image Computing and Computer-Assisted Intervention, 2007, 9 pages.
Riggs, Kyle W. et al., "3D-printed models optimize preoperative planning for pediatric cardiac tumor debulking", Transl Pediatr.; 7(3), Jul. 2018, 10 pages.
Ronneberger, Olaf et al., "U-net: Convolutional networks for biomedical image segmentation", International Conference on Medical Image Computing and Computer-Assisted Intervention, May 2015, 8 pages.
Rueckert, D. et al., "Nonrigid Registration Using Free-Form Deformations: Application to Breast MR Images", IEEE Transactions on Medical Imaging, vol. 18, No. 8, Aug. 1999, 10 pages.
Sermanet, Pierre et al., "Integrated Recognition, Localization and Detection using Convolutional Networks", International Conference on Learning Representations (ICLR2014), Feb. 2014, 16 pages.
Szegedy, Christian et al., "Deep Neural Networks for Object Detection", Adv Neural Inf Process Syst 2013; 26:2553-2561, 2013, Abstract.
Tran, Phi V. , "A fully convolutional neural network for cardiac segmentation in short-axis mri", arXiv preprint arXiv:1604.00494, 2016, 21 pages.
Zhuang, X. et al., "A registration-based propagation framework for automatic whole heart segmentation of cardiac mri", IEEE transactions on medical imaging 29(9), 2010, 14 pages.
"19th Annual Scientific Sessions, Final Program", Society for Cardiovascular Magnetic Resonance, Jan. 27-30, 2016, 90 pages.
"Proceedings of CMR 2018 a Joint EuroCMR/SCMR Meeting", Jan. 31, 2018, 1504 pages.
Akkus, Zeynettin et al., "Deep Learning for Brain MRI Segmentation: State of the Art and Future Directions", J Digit Imaging 30:449-459, Jun. 2, 2017, 11 pages.
Bramlet, Matthew et al., "Multicontrast 3D automated segmentation of cardiovascular images", Journal of Cardiovascular Magnetic Resonance, 18 (suppl 1):O114, Jan. 27, 2016, 2 pages.
Chen, Chen et al., "Deep Learning for Cardiac Image Segmentation: A Review", Frontiers in Cardiovascular Medicine, Mar. 5, 2020, 33 pages.
De Marvao, Antonio et al., "Effect of rare variants in Hypertrophic Cardiomyopathy genes on cardiac morphology in health and disease using machine-learning of CMR", Proceedings of CMR 2018 a Joint EuroCMR/SCMR Meeting, Jan. 31, 2018, 3 pages.
Urbain, Kevin et al., "A fully automated myocardium segmentation from 3D Cardiovascular MR images", CMR 2018—a Joint EuroCMR/SCMR Meeting Abstract Supplement, Jan. 31, 2018, 2 pages.
Zhou, Xiangrong et al., "Deep learning of the sectional appearances of 3D CT images for anatomical structure segmentation based on an FCN voting method", Med. Phys. 44 (10), Oct. 2017, 13 pages.
Zreik, Majd et al., "Deep learning analysis of the myocardium in coronary CT angiography for identification of patients with functionally significant coronary artery stenosis", Medical Image Analysis 44, Nov. 2017, 14 pages.

* cited by examiner

```
┌─────────────────────────────────────────────────────────────────┐
│ Obtaining a trained three-dimensional dataset comprising a first │
│ plurality of two-dimensional images covering a first volume of a │
│ training subject, wherein the trained three-dimensional dataset  │
│ is based upon one or more first magnetic resonance imaging scans │
│ of the training subject                                     902  │
└─────────────────────────────────────────────────────────────────┘
                                  │
                                  ▼
┌─────────────────────────────────────────────────────────────────┐
│ Obtaining an input three-dimensional dataset comprising a second │
│ plurality of two-dimensional images covering a second volume of  │
│ a patient, wherein the input three-dimensional dataset is based  │
│ upon one or more second magnetic resonance imaging scans of the  │
│ patient                                                     904  │
└─────────────────────────────────────────────────────────────────┘
                                  │
                                  ▼
┌─────────────────────────────────────────────────────────────────┐
│ Cropping the input three-dimensional dataset to generate a       │
│ cropped three-dimensional dataset comprising a third plurality   │
│ of two-dimensional images covering a third volume of the patient,│
│ wherein the third volume is smaller than the second volume  906  │
└─────────────────────────────────────────────────────────────────┘
                                  │
                                  ▼
┌─────────────────────────────────────────────────────────────────┐
│ Applying bias field correction to the cropped three-dimensional  │
│ dataset to generate a corrected three-dimensional dataset        │
│ comprising a fourth plurality of two-dimensional images          │
│                                                             908  │
└─────────────────────────────────────────────────────────────────┘
                                  │
                                  ▼
┌─────────────────────────────────────────────────────────────────┐
│ generating a segmented three-dimensional dataset comprising a    │
│ fifth plurality of two-dimensional images, wherein the segmented │
│ three-dimensional dataset further comprises one or more markings │
│ indicating an anatomical structure within the third volume, and  │
│ wherein the segmented three-dimensional dataset is generated via │
│ a convolutional neural network based upon the corrected          │
│ three-dimensional dataset and based upon the trained             │
│ three-dimensional dataset                                   910  │
└─────────────────────────────────────────────────────────────────┘
```

APPARATUS AND METHOD FOR PRODUCING THREE-DIMENSIONAL MODELS FROM MAGNETIC RESONANCE IMAGING

CROSS-REFERENCE TO RELATED APPLICATION(S)

The present application claims the benefit of priority to U.S. Provisional Application No. 62/615,464, filed on Jan. 10, 2018, which is hereby incorporated by reference in its entirety.

FIELD OF THE DISCLOSURE

The subject disclosure relates generally to an apparatus and a method for producing three-dimensional (3D) models from Magnetic Resonance Imaging (MRI). In one specific example, the three-dimensional models can comprise models in the form of or one or more datasets (e.g., which can be displayed on a display screen and/or printed on paper or the like). In another specific example, the three-dimensional models can comprise models in the form of physical 3D models (e.g., 3D printed models).

BACKGROUND

Anatomical models have applications in clinical training and surgical planning as well as in medical imaging research. In the clinic, the physical interaction with models facilitates learning anatomy and how different structures interact spatially in the body. Simulation-based training with anatomical models reduces the risks associated with surgical interventions [McGaghie W C, Issenberg S B, Petrusa E R, Scalese R J. A critical review of simulation-based medical education research: 2003-2009. Med Educ. Wiley Online Library; 2010; 44: 50-63. pmid:20078756], which are directly linked to patient experience and healthcare costs. In addition, the phantoms can be used for pre-operative surgical planning. Lastly, anatomical phantoms can be designed to mimic tissue when imaged with the modality of interest, such as MRI.

Accessibility to 3D printers and advanced segmentation algorithms have led to an increase in use of 3D printing in medicine, which has received interest due to a multitude of potential medical applications. Models can be made patient-specific, and rapidly redesigned and prototyped, providing an inexpensive alternative to generic commercially available anatomical models.

Three-dimensional interaction with patient-specific complex congenital heart defects provide an improved understanding of the problem within the medical decision making pathway. Current medical imaging techniques can generate 3D imaging maps of the chest cavity based on signal intensity or tissue density. The resultant information can be translated into multi-planar reconstruction tools to display two-dimensional (2D) visual representations of the anatomy. Clinicians are trained to recognize the complex patterns of the 2D visual outputs to understand the anatomy and pathophysiology represented in the data. However, the translation of the 2D sequential data to a 3D digital model requires manual segmentation of the clinically relevant components by an experienced reviewer. A current problem with achieving soft tissue segmentation is that automated organ definition remains limited to high contrast data sets such as that which occurs in x-ray projection technology where bone or contrast is enhanced in the imaging; however, much of the clinically relevant content within an imaging dataset resides in the soft tissue elements where low contrast changes exist. This lack of high contrast is not a barrier to a trained expert who can visually recognize the difference, but computational analysis is limited to strict definition of signal regardless of context. Therefore, the manual segmentation of soft tissue organs has typically been the only way to generate a 3D model of clinically relevant anatomy and pathophysiology for such soft tissue organs. In essence, the clinician through manual segmentation of soft tissue creates a 3D digital model based upon their expertise from the 2D sequential imaging dataset. The process typically requires highly specific, and expensive, thresholding computer applications and relies heavily on the clinician's ability to draw out the segments on each of the 2D imaging datasets. This process introduces many opportunities for human error and is time consuming. By automating the process of myocardial and vessel wall segmentation (as described herein in connection with various embodiments), the accessibility and quality of patient specific 3D modeling technology can be dramatically improved.

Deep learning is an arising technique in the field of machine learning, showing promising performance in many artificial intelligence problems such as object detection, recognition, segmentation and so on. Various embodiments described herein employ a pipeline using an existing network structure called U-net [Ozgun cicek, Ahmed Abdulkadir, Soeren S. Lienkamp, Thomas Brox, Olaf Ronneberger. 3D U-Net: Learning Dense Volumetric Segmentation from Sparse Annotation. arXiv:1606.06650 [cs.CV]]. The U-net structure has a contracting path for feature extraction at different scales and an associated expansive path with concatenating of high resolution features for accurate localization. However, this existing method exploits the network to directly learn the non-linear relation between the magnetic resonance MR images and segmentation labels. A non-ideal experimental condition, specifically the bias field, can be introduced by scan parameters and coil sensitivities. The bias field can complicate the relationship between signal intensity variation across the imaging volume and the tissue type, thus complicating the non-linear relationship being learned in deep learning and making the learning problem harder.

BRIEF DESCRIPTION OF THE DRAWINGS

Reference will now be made to the accompanying drawings, which are not necessarily drawn to scale, and wherein:

FIG. 3A depicts a set of representative slices of the cropped heart images with bias field correction. FIG. 3B depicts a corresponding set of representative slices of the cropped heart images without bias field correction. FIG. 3C depicts the associated bias field estimated from the multiplicative intrinsic component optimization (MICO) method.

FIG. 4A depicts myocardium labels from automated segmentation with bias field correction. FIG. 4B depicts myocardium labels from automated segmentation without bias field correction. FIG. 4C depicts myocardium labels from manual segmentation.

FIG. 5 depicts coded myocardium labels overlaid on top of the magnitude images.

FIG. 9 depicts a method according to an embodiment.

DETAILED DESCRIPTION

With the increased utility of 3D modeling in medicine, an increase in segmentation efforts through specialized software has increased. However, most segmentation software focuses on signal intensity values that are in stark contrast to other tissue values. Segmentation solutions that focus on bone or intravenous contrast are well established, however, the clinical value of medical images more frequently relies on the trained physician's understanding of the slight signal intensity changes of soft tissues. As described herein, various embodiments enable automated creation of soft tissue segmentations replicating the trained physician's eye which goes beyond signal intensity to relational to the expected 3D form of human anatomy.

As described herein, various embodiments provide for creating 3D models of organs from imaging data. In one specific example, a method of an embodiment can comprise: acquiring a set of image data of an organ of interest using an imaging modality, cropping images of the organ of interest from the full set of image data, correcting one or more non-ideal experimental conditions, labeling a set of coordinates (e.g., myocardium coordinates) from the cropped images using a deep learning technique, and translating the set of labeled coordinates (e.g., myocardium coordinates) to produce a three-dimensional model.

Figure 1:
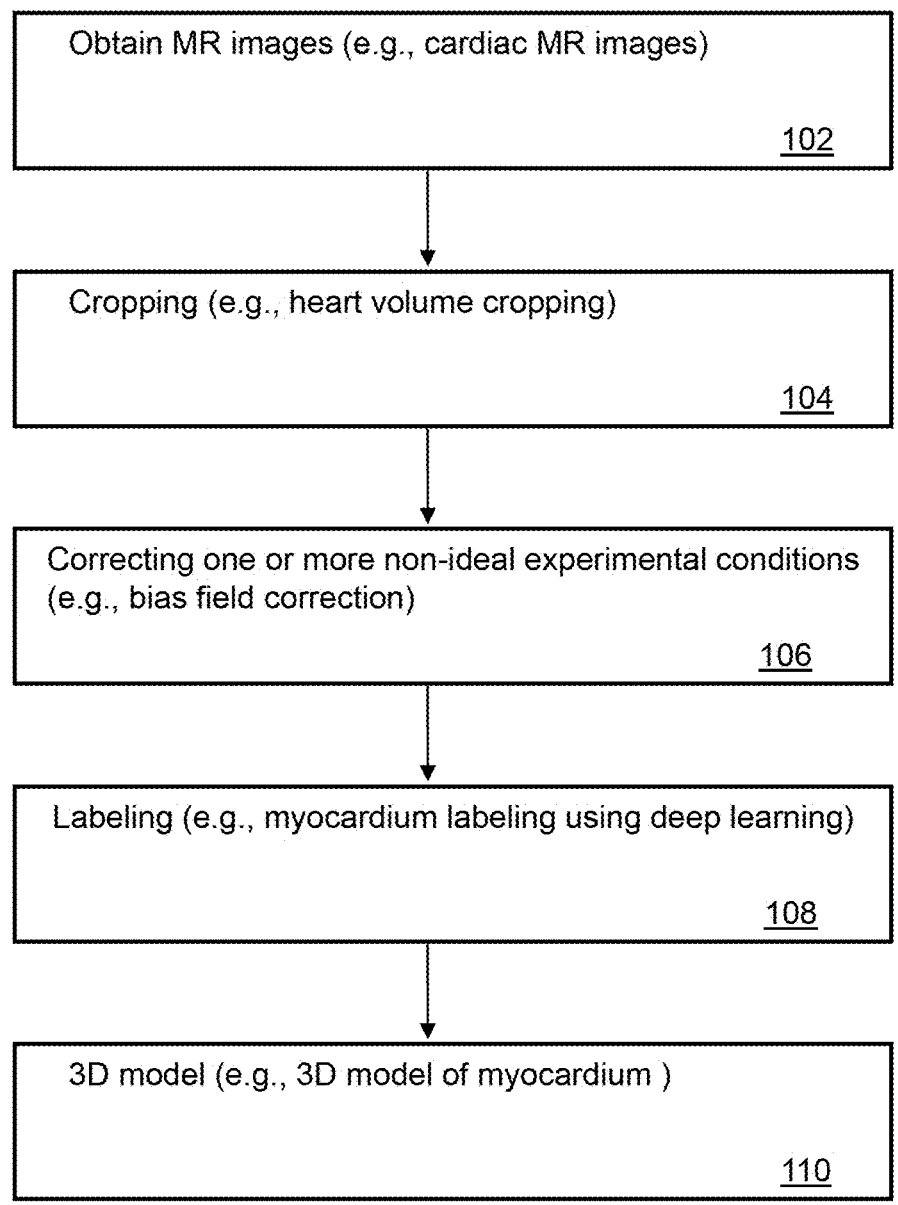
FIG. 1 depicts a schematic overview of a workflow approach according to an embodiment (wherein the workflow is in connection with an automated cardiac segmentation pipeline).

As described herein, various embodiments provide a fully automated pipeline to generate 3D digital heart models directly from magnetic resonance (MR) scans. The process can be a critical step in creating patient-specific heart models for pre-surgery planning in children and adults with complex congenital heart disease (CHD). In an embodiment, cardiac MR images of a patient are obtained from an MR scanner (see, e.g., block 102 of the workflow of FIG. 1). Then, the obtained MR images are sent through the automated segmenting pipeline consisting of several sequential procedures, including heart volume cropping (see, e.g., block 104 of FIG. 1), correcting one or more non-ideal experimental conditions (see, e.g., block 106 of FIG. 1), and myocardium labeling using deep learning (see, e.g., block 108 of FIG. 1). Finally, the coordinates of myocardium regions from the imaging sequence are translated into an accurate 3D digital model of the heart (see, e.g., block 110 of FIG. 1). The 3D digital model can then be utilized (e.g., by a clinician) in various formats such as physical 3D print format and/or digital format for virtual, mixed, and/or augmented reality applications. Automated segmentation of the heart muscle is challenging because of surrounding structures, such as the liver and chest wall, which have signal intensity that is very similar to the heart muscle signal.

There are several features associated with various embodiments: 1) Correction for non-ideal experimental condition. The non-ideal experimental condition (e.g., bias field modulating signal intensity across the heart) existing in practical scans may complicate the nonlinear mapping between the cardiac MR image intensities and the myocardium labels. With the non-ideal experimental condition removed or alleviated before training a machine learning algorithm, the performance of deep learning based segmentation is significantly improved. 2) Heart volume cropping. Conventional registration based method is adopted to roughly crop a smaller volume containing the heart from the full imaging volume in order to reduce the complexity of the problem. 3) A U-Net deep learning algorithm is trained on a variety of images of differing ages and sizes of subjects (the algorithm performs well on a range of sizes of subject's hearts). 4) The method of an embodiment provides a quick and accurate segmentation without required user intervention.

Various embodiments enable distribution of this highly specific and specialized task to many more medical institutions through an automated process obviating expense, time, and training needed to develop the internal competency to deploy this valuable process within medical decision making pathways.

In one embodiment, heart cropping can utilize a non-rigid registration method [D. Rueckert et al. "Nonrigid Registration Using Free-Form Deformations: Application to Breast MR Images". IEEE Tran Med Imaging 1999; 18:712-721] to localize the target heart volume. In this embodiment, given a reference cardiac dataset and manually selected heart volume, the transform is first estimated from reference space to target space, and then the estimated transformation is used to convert the reference heart volume to the target space. The reference heart volume comes with a mask indicating the location of the heart.

With regard now to bias field correction, it is noted that performance of a deep learning based method typically depends on the complexity of the underlying nonlinear mapping of signal intensity and label of structure [see, for example: LeCun Y, Kavukcuoglu K, Farabet C. Convolutional networks and applications in vision. In Proceedings of IEEE International Symposium on Circuits and Systems (ISCAS). 2010. p 253-256; Szegedy C, Toshev A, Erhan D. Deep neural networks for object detection. Adv Neural Inf Process Syst 2013; 26:2553-2561; Sermanet P, Eigen D, Zhang X, Mathieu M, Fergus R, LeCun Y. Overfeat: integrated recognition, localization and detection using convolutional networks. International Conference on Learning Representations (ICLR2014), 2014; Krizhevsky A, Sutskever I, Hinton G E. Image net classification with deep convolutional neural networks. Adv Neural Inf Process Syst 2012:1097-1105]. Thus, preprocessing is typically necessary to exclude factors that may complicate the nonlinear relationship. Specifically, in an embodiment, bias field correction [Chunming Li, John C. Gore, Christos Davatzikos. Multiplicative intrinsic component optimization (MICO) for MRI bias field estimation and tissue segmentation, Magn Reson Imaging 2014; 32: 913-923] is used to reduce the signal intensity variation induced by the MR sequence and coils between scans. This bias field correction is performed (in this embodiment) before training the algorithm, providing a pre-processing for the deep learning based method.

Reference will now be made to myocardium segmentation according to an embodiment. In this embodiment, after bias field correction, a convolutional neural network is exploited to obtain myocardium labels from the images. In one specific example, a CNN with contracting path and expansive path using U-net structure [Özgün cicek, Ahmed Abdulkadir, Soeren S. Lienkamp, Thomas Brox, Olaf Ronneberger. 3D U-Net: Learning Dense Volumetric Segmentation from Sparse Annotation. arXiv:1606.06650 [cs.CV]] are used. The contracting path with pooling enables large receptive field (i.e., use of context) and superior feature extraction ability while the expansive path with concatenating of high resolution features from contracting path ensures high localization accuracy. Using the imaging data, 3D models can then be printed on a 3D printer.

As described herein, in one embodiment an overall process can operate as follows: (1) Training of a machine learning algorithm with manually labeled clinical data denoted by expert. This involves, in one example, applying an image processing pipeline such as described herein (see, e.g., FIG. 1). The image processing pipeline can include cropping and bias field correction to get original images to look like the images that will eventually be classified. However, these manually labeled data also have the "ground truth" answer with them. These prepared images and the ground truth segmentation are given to the machine learning algorithm in the "learning" stage and the machine learning algorithm trains on these images. In one example, the training data can be supplemented (to increase the number of datasets used in training) by using shearing and rotations. This process of modifying data for reuse in training is called data augmentation. (2) Once the machine learning (e.g., deep learning) algorithm is trained, the machine learning algorithm can be given novel data (untrained data) to segment. In one example, the untrained data must go through the cropping and bias field correction steps to be compatible with the trained algorithm which learned to segment data that already had these nuisance signal effects removed (the extra signal from other regions in the image and the non-uniform weighting of signal intensity across the image). (3) The resulting segmentation can be converted into a 3D object for printing and/or viewing in virtual reality. In one specific example, the resulting segmentation can be compared with manual segmentation by an expert to assess the accuracy and reliability of the method. In another specific example (e.g., related to feedback), the resulting segmentation can be modified by a trained expert in the anatomy to provide a further dataset for further training of the machine learning algorithm.

Still referring to the overall process of one embodiment described above, it is noted that the entire field of view (FOV) of an image typically covers, for example, the whole subject thorax while the heart only resides in a smaller region. To reduce the complexity of the learning method, the recognition problem can be restricted to a local region sufficiently containing the whole heart anatomies via a step referred to as cropping. The cropping step can be conducted manually and/or automatically. Automatic cropping can proceed by using a normative anatomical image in the processing pipeline (such as described herein) to align with the given image and to propagate a mask into the new image's space.

Still referring to the overall process of one embodiment described above, it is noted that magnetic resonance (MR) images are typically affected by the bias field distortion, which is related to the receive coil sensitivity function and the associated coil combination method. This results in variations in intensity for the same tissues at different locations. This interferes with accurate segmentation, so the interference is removed (by bias field correction) prior to training and also in the data (e.g., patient data) for which the machine learning algorithm will be applied. To correct the interference, one implementation is to adopt the multiplicative intrinsic component optimization (MICO) method.

Still referring to the overall process of one embodiment described above, it is noted that in one specific example described herein the "ground truth" creation was produced as follows. In particular, in this example, the 3D cardiovascular MR datasets include a variety of congenital heart defects, which were collected from CHD patients using a balanced steady-state-free-precession (bSSFP) pulse sequence (TR=3.93 ms, TE=1.65 ms, TI=47 ms, FA=65°, voxel size=1.1×1.1×2.6 mm 3, FOV, Bandwidth/Pixel) on a 1.5T GE scanner with IRB (Institutional Review Board or Ethics Oversight Board) approval. The scans were acquired using ECG and respiratory-navigator gating. Annotated reference myocadium labels were obtained by manual delineation of the myocardium by an experienced clinician. Each case approximately takes two hours to manually label using software such as Mimics software (Materialise Inc.).

Still referring to the overall process of one embodiment described above, it is noted that a comparison to "ground truth" was performed as follows. The DICOM data from the MRI scanner of this example were sent directly to the algorithm for segmentation using the trained machine learning algorithm and processing pipeline such as described herein. In addition, a clinical expert manually segmented several datasets. A comparison between the automated and expert manual segmentation was performed to determine performance of the machine learning and processing pipeline algorithm. The evaluation of the segmentation exploits four metrics: Dice Similarity Coefficient (DSC), Positive Predictive Value (PPV), Sensitivity, and Hausdorff Distance of Boundaries (Hdb[mm]), considering both region and boundary similarities.

Still referring to the overall process of one embodiment described above, it is noted that output of a 3D model can be performed as follows. The autosegmentation method of this example will output a 3D model with binary mask, where 1 indicates myocardium tissues, 0 indicates non-myocardium tissues including the background. This 3D model can be saved in a variety of formats including .STL. This STL file can be used in 3D printing and/or in viewing in a VR system.

In an example use, a clinical site would take an image processing pipeline such as described herein, the applicable computer code to interface with the trained machine learning algorithm, and the trained machine learning algorithm (including the structure, weights, and computations that are set up for this problem and also that are learned). In this example, the clinical site would execute the pipeline on their data from their MRI scanner and get 3D models directly out of the pipeline without manual user intervention required. In another example, the clinical site would execute the pipeline on their data from their computerized tomography (CT) scanner and get 3D models directly out of the pipeline without manual user intervention required.

As described herein are various embodiments directed to Myocardium Segmentation for Patients with Congenital Heart Disease Using CNN from 3D Cardiovascular MR Images. In this regard, presurgical planning for congenital heart disease (CHD) requires precise knowledge of the subject specific anatomy. This anatomical information is available from cardiovascular MR (CMR), but segmentation of the heart tissue from the rest of the structures in the image takes a skilled viewer several hours per dataset. Various embodiments provide an automatic method using deep convolutional neural networks (CNNs) for segmentation of the myocardium in CMR of patients with CHD.

In one specific example, as described herein, thirty training and ten test CMR scans were obtained from CHD patients. A deep encoding-decoding CNN with skip connections was trained for myocardium segmentation for 3D volumes. Performance was evaluated within patient data with manual segmentation. Automatic segmentation of the test scans was very accurate, resulting in Dice indices of 0.847, positive predictive value of 0.763, and sensitivity of 0.952 for the myocardium. Segmentation took 20 s per 3D volume using a workstation with graphics processing unit (GPU).

Congenital heart disease (CHD) is a type of congenital defect affecting almost 1% of live births [Hoffman J L, Kaplan S. The incidence of congenital heart disease. J Am Coll Cardiol. 2002; 39(12):1890-1900]. Patients with CHD often require surgery in their childhood. It has been shown that the use of patient-specific 3D models is helpful for preoperative planning [Kyle W. Riggs, Gavin Dsouza, John T. Broderick, Ryan A. Moore, and David L. S. Morales. 3D-printed models optimize preoperative planning for pediatric cardiac tumor debulking. Transl Pediatr. 2018 July; 7(3): 196-202]. Such models are typically based on a segmentation of the patient's anatomy in cardiovascular MR (CMR). However, segmentation of cardiac structures in CMR requires several hours of manual annotations. Hence, there is a need for semi-automatic or fully automatic segmentation methods to speed up this time-consuming process and reduce the workload for clinicians.

Due to the low tissue contrast of the myocardium against surroundings, patient variability and spatial inhomogeneities, it is very challenging to develop automatic solutions for efficient whole heart segmentation. Based on ad hoc features, previous automatic methods typically exploited deformable models [[Peters, J., Ecabert, O., Meyer, C., Schramm, H., Kneser, R., Groth, A., Weese, J. Automatic whole heart segmentation in static magnetic resonance image volumes. In: International Conference on Medical Image Computing and Computer-Assisted Intervention. pp. 402-410. Springer (2007)], non-rigid registration [Zhuang, X., Rhode, K. S., Razavi, R. S., Hawkes, D. J., Ourselin, S.: A registration-based propagation framework for automatic whole heart segmentation of cardiac mri. IEEE transactions on medical imaging 29(9), 1612-1625 (2010)] and expert involved interactive segmentation [Pace, D. F. Dalca, Geva, T Powell, A. J., Moghari, M. H., Golland, P.: Interactive whole-heart segmentation in congenital heart disease. in: International Conference on Medical image Computing and Computer-Assisted Intervention. pp. 80-88. Springer (2015)]. Renowned for their powerful feature learning capabilities, Convolutional Neural Networks (CNNs) have been utilized in a 2D context for biomedical image segmentation [Ronneberger. O., Fischer, P., Brox, T.: U-net: Convolutional networks for biomedical image segmentation. In: International Conference on Medical image Computing and Computer-Assisted Intervention. pp. 234-241. Springer (2015)] and ventricle segmentation [Tran, P. V.: A fully convolutional neural network for cardiac segmentation in short-axis mri. arXiv preprint arXiv:1604.00494 (2016)]. However, leveraging the effectiveness of CNNs in capturing 3D spatial contextual information to segment the whole heart from MRI volumes has not been well studied. Recently, dense volumetric labeling has attracted attention in medical image computing community [Özgün Çiçek, Ahmed Abdulkadir, Soeren S. Lienkamp, Thomas Brox and Olaf Ronneberger. 3d u-net:Learning dense volumetric segmentation from sparse annotation. arXiv preprint arXiv:1606.06650 (2016); Dou, Q., Chen, H., Jin, Y., Yu, L., Qin, J., Heng, P. A.: 3d deeply supervised network for automatic liver segmentation from ct volumes. arXi.v preprint arXiv:1607.00582 (2016); [9] Merkow, J., Kriegman, D., Marsden, A. Tu, Z.: Dense volume-to-volume vascular boundary detection. arXiv preprint arXiv:1605.08401 (2016)]. Recent efforts are focused on how to construct more effective networks that can be trained more efficiently, and how to distill hierarchical features to enable better performance.

As mentioned above, deep learning is an emerging technique in the field of machine learning, showing promising performance in many artificial intelligence problems such as object detection, recognition, segmentation and other applications. A pipeline described herein according to an embodiment used an existing network structure called U-net. The U-net structure has a contracting path for feature extraction at different scales and an associated expansive path with concatenating of high resolution features for accurate localization. However, this existing method exploits the network to directly learn the non-linear relation between the MR images and segmentation labels. In an implementation described herein according to an embodiment, the data is prepared to enable a more efficient learning process by correcting for non-ideal experimental conditions. Specifically, in an embodiment, addressed is the bias field (which exists across the image and which is due to the coil sensitivities and other scan parameters). The bias field can complicate the signal intensity variation across the imaging volume, and thus complicate the non-linear relationship (making the learning problem harder). With a bias field correction procedure described herein according to an embodiment, the performance of the deep learning based method has been improved.

Reference will now be made to certain Methods and Materials according to various embodiments. In particular, reference will now be made to Datasets associated with an example. The 3D Cardiovascular MR datasets used in this example study include a variety of congenital heart defects, which were collected (as mentioned above) from CHD patients using a balanced steady-state-freeprecession (bSSFP) pulse sequence (TR=3.93 ms, TE=1.65 ms, TI=47 ms, FA=65°, voxel size=1.1×1.1×2:6 mm$^3$, FOV, Bandwidth/Pixel) on a 1.5T GE MRI scanner with IRB (Institutional Review Board or Ethics Oversight Board) approval. The scans were acquired using ECG and respiratory-navigator gating. In total, approximately 38 datasets were provided with annotated reference labels for training and evaluation purposes. The reference labels for the training datasets were obtained by manual delineation of the myocardium by an experienced clinician. Each case approximately takes two hours to manually label using the Mimics software. Due to the small number of datasets available for training, value augmentation (such as rotation, shearing, flipping, elastic transformation) was used to enable the automated segmentation to be invariant to such deformations. The network was trained using a workstation with a NVIDIA TITAN Xp graphic processor unit (GPU) for 3 days. The automated segmentation of an embodiment takes less than 15 minutes on a workstation with an eight core i7 CPU.

Still referring to certain Methods and Materials reference will now be made in particular to Pre-processing associated with an example. Several preprocessing steps conditioned the data to remove non-ideal effects and to provide focus for the segmentation algorithm.

One of these preprocessing steps is Heart cropping: The entire field of view (FOV) covers, in this example, the whole subject thorax while the heart only resides in a smaller region. To reduce the complexity of the learning method, the recognition problem is restricted (e.g., via manual cropping or automatic cropping) to a local region sufficiently containing the whole heart anatomies. The time required for manually cropping is usually on the order of seconds, which is negligible to that required by manual myocardium labeling. Note that an approach of an embodiment described herein can also (or instead) incorporate automatic cropping through registration with a reference anatomy with mask, as described above.

Another one of the preprocessing steps mentioned above is Bias field correction: MR images are affected by the bias field distortion, which is related to the receive coil sensitivity function and the associated coil combination method. This results in variations in intensity for the same tissues at different locations. To correct for it, various embodiments described herein use the multiplicative intrinsic component optimization (MICO) method [Chunming Li, John C. Gore, Christos Davatzikos. Multiplicative intrinsic component optimization (MICO) for MRI bias field estimation and tissue segmentation, Magn Reson Imaging 2014; 32: 913-923]. Also (or instead) applied in various embodiments is contrast normalization (normalize by image mean and standard deviation) as suggested by Adam Coates [A Coates, H. Lee, A. Y. Ng. An analysis of single-layer networks in unsupervised feature learning. Proc. 14$^{th}$ Intl Conf on Artificial Intelligence and Statistics (AISTATS) 2011].

Another one of the preprocessing steps mentioned above is Data Augmentation: In various embodiments, when only few training samples are available, data augmentation is essential to teach the network the desired invariance and robustness properties. In the example study described herein, primarily adopted were rotation invariance as well as robustness to deformations and gray values variations. In particular, random elastic deformations of the training samples seems to be the key concept to train a segmentation network with very few annotated images. Smooth deformations are generated using random displacement vectors on a coarse 3 by 3 grid. The displacements are sampled from a Gaussian distribution with 10 pixels standard deviation. Per-pixel displacements are then computed using bicubic interpolation.

Figure 2:
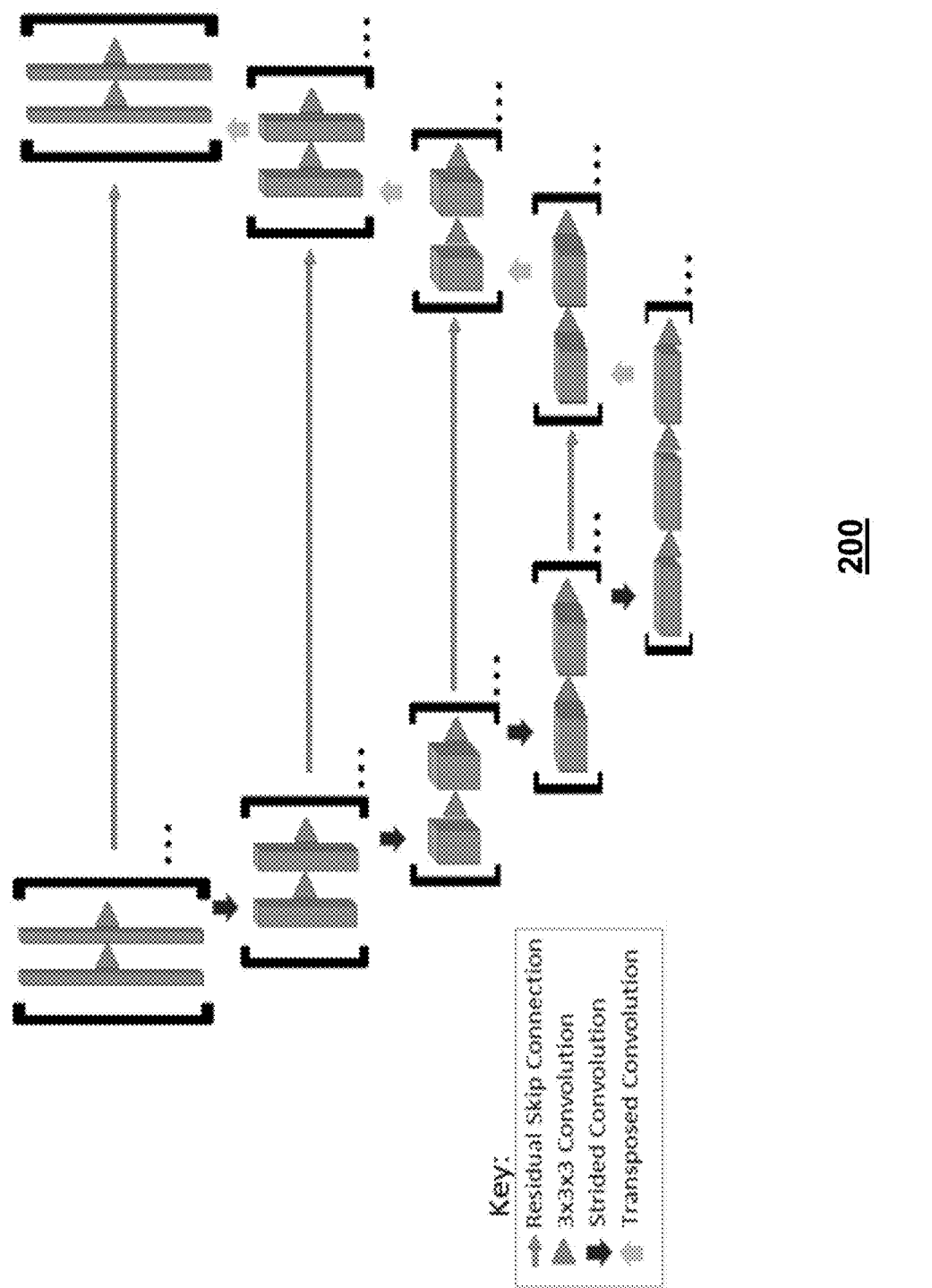
FIG. 2 depicts a network architecture of a deep-CNN (convolutional neural network) for myocardial labeling according to an embodiment. In this FIG. 2, each horizontal arrow represents a residual skip connection; each small, right-facing triangle icon represents a 3×3×3 convolution; each small, downward-facing arrow represents a strided convolution; and each small, upward-facing arrow represents a transposed convolution.

Still referring to certain Methods and Materials, reference will now be made in particular to Deep-CNN based Segmentation associated with an example. FIG. 2 illustrates, according to an embodiment, the architecture of a deeply supervised 3D CNN for dense volumetric whole heart segmentation. It employs 3D CNN, DeCNN, skip connection and a fully connected layer. Discussed below are elaborations of certain technical details of the networks, certain details of the 3D CNN, and certain details of the deep supervision scheme which is used to tackle potential optimization difficulties in training the whole deep CNN. Specifically, a CNN with contracting path and expansive path using U-net structure is used in this embodiment. The contracting path with pooling enables large receptive field (i.e., use of context) and superior feature extraction ability while the expansive path with concatenating of high resolution features from contracting path ensures high localization accuracy.

Still referring to Deep-CNN based Segmentation associated with an example, reference will now be made in particular to Convolutional Layer. CNNs of this embodiment are constructed by repeatedly applying convolutional layer to previous feature maps, extracting high-level features to predict myocardium labels. The i-th convolutional layer can be expressed as:

$$C_i = \varphi(\omega_i * f_{i-1} + b_i) \tag{1}$$

where $f_{i-s}$ is the previous feature map, $\omega_i$ the current convolutional kernel (e.g., of size 3×3×3), $b_i$ the bias constant in the current convolutional layer and p the nonlinear activation function (e.g., ReLU $\{\varphi(x)=\max(x, 0)\}$ in this study). The convolutional layer is used to extract high-level features from previous feature maps at the cost of resolution reduction.

Still referring to Deep-CNN based Segmentation associated with an example, reference will now be made in particular to Deconvolutional Layer. To restore the resolution reduction after the convolution operation, deconvolutional layer (namely transposed convolution) is adopted. The deconvolutional layer can be expressed as:

$$C_i = \varphi(\omega_i^c * f_{i-1} + b_i) \tag{2}$$

where $f_{i-s}$ is the previous feature map, $\omega_i^c$ the deconvolutional kernel (e.g., 3×3×3), $b_i$ the bias constant and $\varphi$ the nonlinear activation function (e.g., ReLU in this study). As can be seen, the difference between convolutional layer and deconvolutional layer is the kernel weights.

Still referring to Deep-CNN based Segmentation associated with an example, reference will now be made in particular to Skip connection. Skip connection is employed to create a pathway for high resolution information to be delivered to the corresponding low resolution feature at the same scale. This enables high localization of the previous feature maps to be incorporated with the high-level features to provide accurate label prediction. In general, there are two ways of skip connection: cascade and summation. In this embodiment, a cascade connection is employed.

Still referring to Deep-CNN based Segmentation associated with an example, reference will now be made in particular to Fully connected layer: At the end of the network, a 1×1×1 convolutional layer is added as a main classifier to generate the segmentation results and further get the segmentation probability volumes after passing the soft-max layer.

Still referring to Deep-CNN based Segmentation associated with an example, reference will now be made in particular to Softmax loss layer. The energy function is computed by a pixel-wise soft-max over the final feature map combined with the cross entropy loss function. The soft-max is defined as:

$$p_k(x) = \frac{\exp(\alpha_k(x))}{\sum_{k'=1}^{K} \exp(\alpha_{k'}(x))} \tag{3}$$

where $\alpha_k(x)$ denotes the activation in feature map k at the pixel location x. The cross entropy then penalizes at each position the deviation of $p_{l(x)}(x)$ from 1 using:

$$E = \sum_{x \in \Omega} m(x) \log(p_{l(x)}(x)) \tag{4}$$

where l(x) is the true label of each pixel and m(x) is a weight map that introduced to give some pixels more importance in the training. The weight map was pre-calculated to balance the class frequencies, i.e., inverse proportional to the number of each class labels.

Reference will now be made to certain Experiments according to various embodiments. In particular, reference will now be made to Implementation Details associated with an example. In this example, the method was implemented with C++ and Matlab under the open source deep learning library of Caffe [Yangqing Jia, Evan Shelhamer, Jeff Donahue, Sergey Karayev, Jonathan Long, Ross Girshick, Sergio Guadarrama, Trevor Darrell. Caffe: Convolutional Architecture for Fast Feature Embedding. Proceedings of the 22nd ACM international conference on Multimedia Pages 675-678], using a workstation with a 3.30 GHz Intel Core i9-7900X CPU and a NVIDIA TITAN X GPU. The weights of networks were initialized from a Gaussian distribution $$(\mu=0, \sigma=\sqrt{2/n}),$$

where n denotes the number of incoming nodes. The weights were updated using stochastic gradient descend (SGD) method with batch size 1, momentum 0.9 and weight decay $10^{-3}$. The learning rate was set as $2\times10^{-3}$ initially and reduced by a factor of 0.8 every 4000 iterations. The network was trained for up to $2\times10^5$ iterations. For training, a 127×127×63 sub-volume was randomly cropped on the fly (from the original heart images) for the input in every iterations from each sample with "zero" extrapolation if needed. 3D rotation, elastic deformation and other value augmentation were also conducted on the fly to provide more sample variant for training. The transformation parameters were randomly selected from a reasonable range (rotation angle from 30° to −30°, white value from 0.95 to 1.05). For testing, an overlap-tiling strategy was used to generate the whole volume probability map by stitching subvolume predictions. Lastly, morphology operation such as region growing was performed to eliminate isolated outliers. Generally, it took about 12 seconds to classify one volume with size about 127×127×63 using above configuration.

Still referring to certain Experiments, reference will now be made in particular to Evaluation associated with an example. The evaluation of the segmentation exploits four metrics: Dice Similarity Coefficient (DSC), Positive Predictive Value (PPV), Sensitivity, and Hausdorff Distance of Boundaries (Hdb[mm]), considering both region and boundary similarities. The DSC measures the similarity (i.e., overlap between the manual and the automatic myocardium labels). It is defined as:

$$DSC = \frac{2TP}{FP + 2TP + FN} \quad (5)$$

where TP, FP and FN are the numbers of true positive, false positive and false negative detections, respectively. The PPV measures the amount of TP over all positive predictions:

$$PPV = \frac{TP}{TP + FP} \quad (6)$$

Sensitivity is to measure the ability to determine the myocardium tissue correctly, which is defined as:

$$Sensitivity = \frac{TP}{TP + FN} \quad (7)$$

Finally, the Hdb measures how far the manual and the automatic myocardium boundaries are from each other. Let X and Y be the two myocardium boundaries of a certain metric space, the Hdb $d_H$ (X; Y) is defined by:

$$d_H(X, Y) = \max\left\{\sup_{x \in X} \inf_{y \in Y} d(x, y), \sup_{y \in Y} \inf_{x \in X} d(x, y)\right\} \quad (8)$$

where sup represents the supremum and inf the infimum. For DSC, PPV and Sensitivity, higher values indicate better performance. While for Hdb, lower values indicate better performance.

Still referring to certain Experiments, reference will now be made in particular Results associated with an example. Training was performed on 20 datasets which were manually segmented by a trained rater. For testing, 5 datasets were held out of the training and this data was used exclusively for testing the performance of the algorithm on data that was not trained on. Tables I and II below enumerate certain results.

TABLE I

Quantitative evaluation results of the training

| Subject | DSC | PPV | Sensitivity |
|---------|-----|-----|-------------|
| CM0002 | 0.847 | 0.763 | 0.952 |
| CM0004 | 0.859 | 0.779 | 0.956 |
| CM0006 | 0.840 | 0.751 | 0.953 |
| CM0013 | 0.856 | 0.769 | 0.965 |
| CM0021d | 0.836 | 0.745 | 0.952 |
| CM0021s | 0.831 | 0.729 | 0.965 |
| CM0027 | 0.718 | 0.570 | 0.971 |
| CM0051 | 0.774 | 0.644 | 0.971 |
| CM0053 | 0.827 | 0.722 | 0.967 |

TABLE II

Quantitative evaluation results of the testing datasets

| Subject | DSC | PPV | Sensitivity |
|---------|-----|-----|-------------|
| CM0069 | 0.690 | 0.614 | 0.788 |
| CM0070 | 0.653 | 0.543 | 0.821 |
| CM0073 | 0.653 | 0.553 | 0.797 |
| CM0074 | 0.667 | 0.545 | 0.857 |

Figures 3A, 3B, 3C:
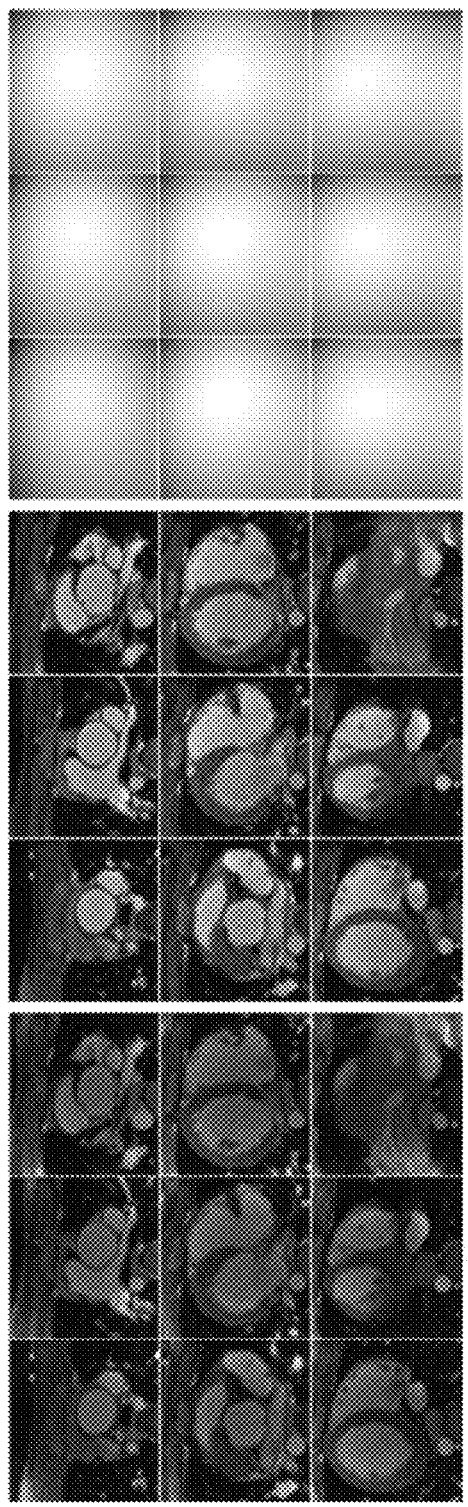
FIGS. 3A-3C depict certain images according to various embodiments.
Figures 4A, 4B, 4C:
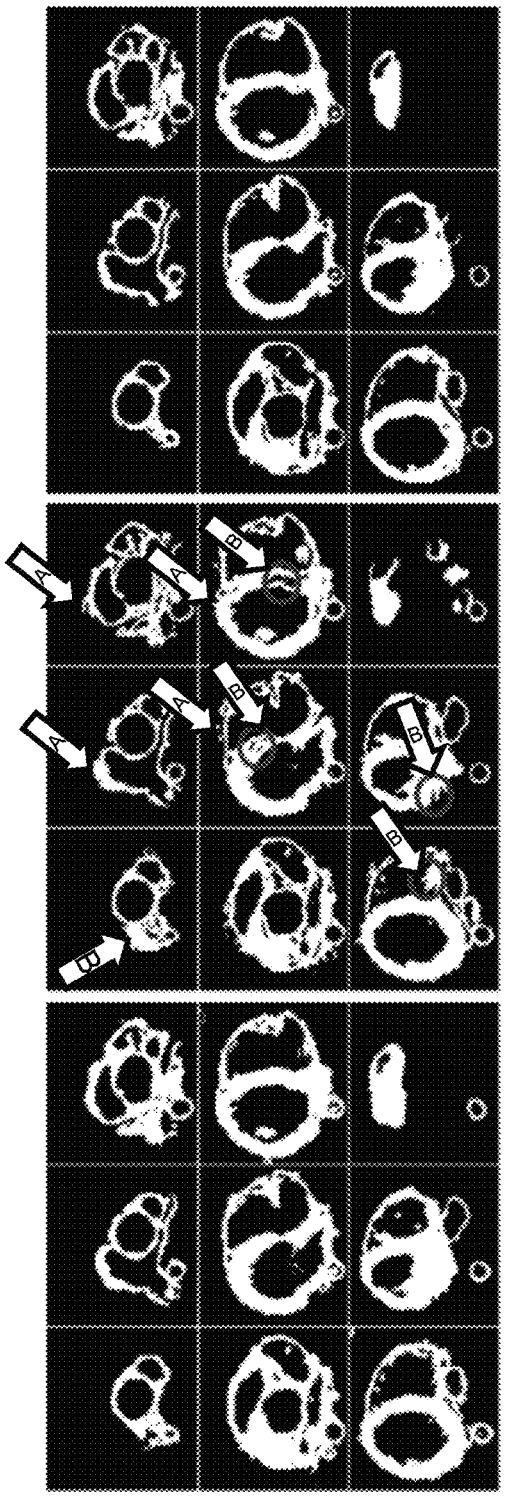
FIGS. 4A-4C depict certain images according to various embodiments.
Figure 5:
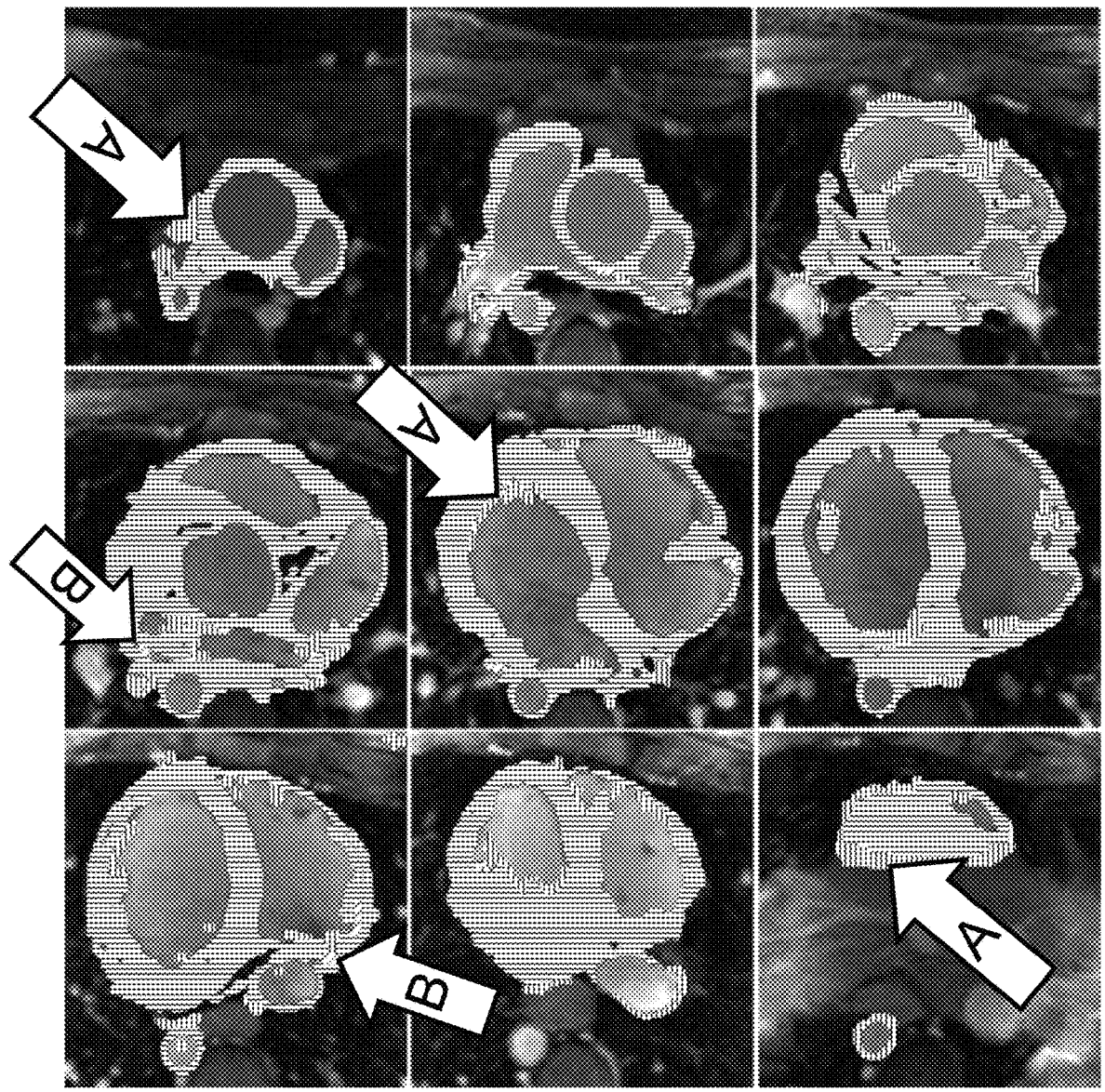
FIG. 5 depicts certain images according to various embodiments. More particularly.

Referring now to FIGS. 3A-3C, 4A-4C and 5, cropped heart images (associated with the data collection mentioned above) with and without bias field correction are shown respectively in FIGS. 3A and 3B, with corresponding myocardium labels shown respectively in FIGS. 4A and 4B. The overall bias field (FIG. 3C) was successfully removed from the raw images, leading to improved differentiation between the myocardium and surrounding tissues (see generally the example arrows labeled "A" in FIG. 4B). The segmentation of myocardium inside the heart are also more accurate after bias field correction (see generally the example arrows labeled "B" in FIG. 4B). To compare the automated segmentation of an embodiment with manual segmentation, both labels were coded and overlaid on the magnitude images (FIG. 5). In FIG. 5, the horizontal shading shows areas of agreement between a fully automated method of an embodiment and manual segmentation. Vertical shading (see generally the example arrows labeled "A" in this FIG. 5) show extra regions captured by the automated method of an embodiment. Diagonal shading (see generally the example arrows labeled "B" in this FIG. 5) show regions not captured by the automated method of an embodiment. As can be seen, both methods reached an agreement in most myocardium regions (~91%). Preliminary results based on patient datasets demonstrate the feasibility of the method according to an embodiment in reducing the intensive labor in traditional manual segmentation.

Figure 6:
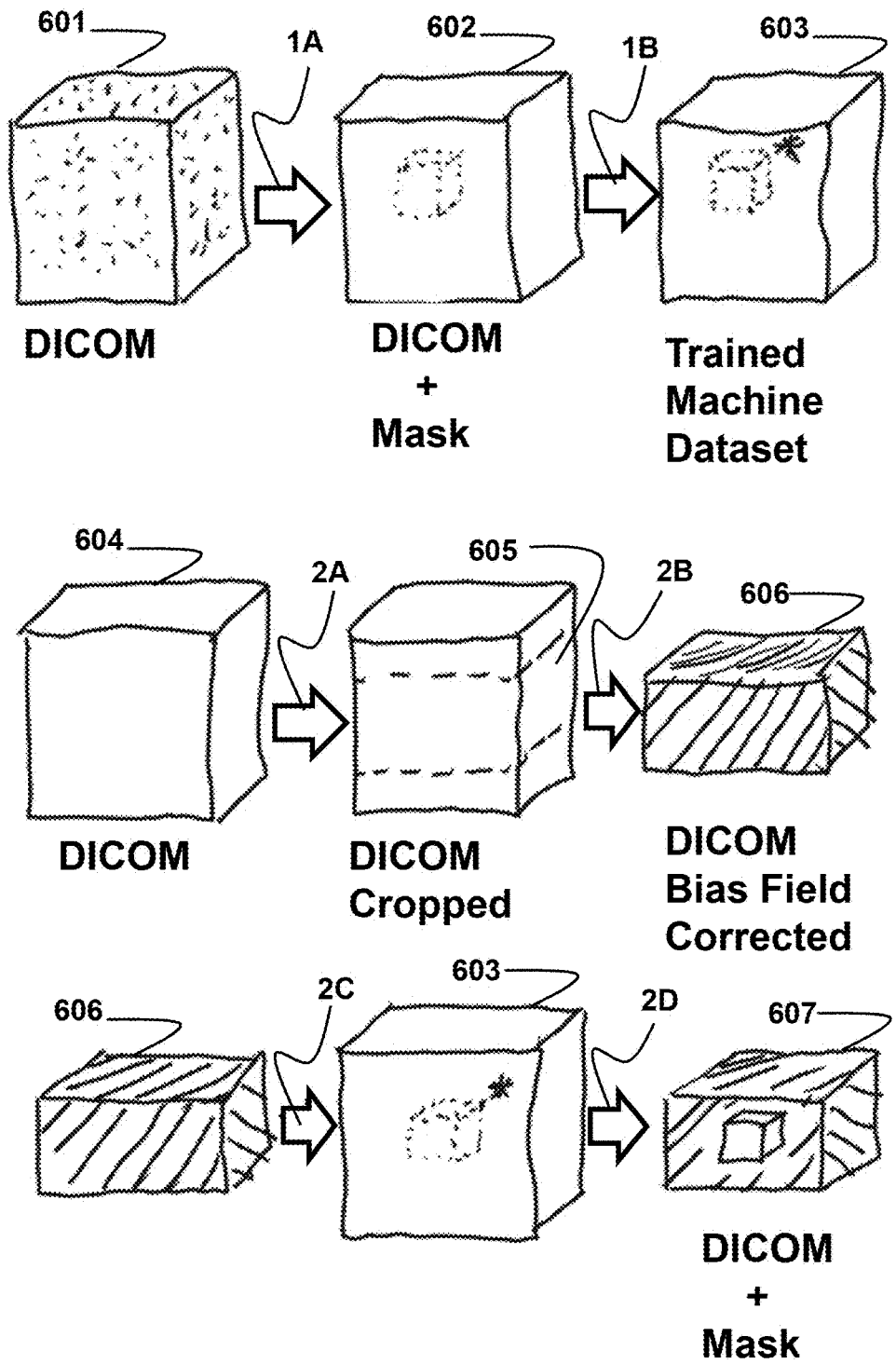
FIG. 6 depicts a graphical representation of processing according to an embodiment.

Referring now to FIG. 6, a graphical representation of processing according to an embodiment is shown. In general, a Digital Imaging and Communications in Medicine (DICOM) dataset is entered into the program, a cropping program is utilized to reshape the DICOM dataset, the new cropped dataset is converted to an alternate signal intensity format through a bias field correction algorithm, and the new alternate signal intensity format dataset (that is, the bias field corrected dataset) is then compared to a previously prepared expert manually trained ground truth dataset where myocardial signal intensity elements (that fall within "ground truth" parameters) are selected in the bias field corrected dataset. Selected voxels (in the bias field corrected dataset) are then assigned to coordinate system in 3D model format and output as both volumetric dataset and 3D file format.

Still referring to FIG. 6, certain specific details of a process for creating a trained machine dataset according to this embodiment are as follows: Block 601—DICOM dataset: voxel based data with each voxel representing a signal intensity value at a fixed coordinate position within the dataset. STEP 1A—a subject matter expert (SME) manually reviews the 3D dataset (block 601) in 2D slices and manually selects regions of interest that correspond to the target segment (e.g., myocardium and vessel wall). This process is repeated slice by slice through the entire 3D block. The result is a DICOM dataset (block 602) with a subset of voxels selected which: (1) Fall within a signal intensity range consistent with the desired target tissue; and (2) Are positioned within the 3D coordinate block consistent with the expected position of the target anatomy (e.g., heart). The importance of this distinction is that there likely are voxels within the signal intensity range that fall outside of the expected position of the target anatomy which are not selected and there likely are voxels which fall within the expected anatomy, but are not of proper signal intensity (anatomy defects). Thus, block 602 is a DICOM dataset with a selected volumetric mask which corresponds to the desired anatomy. STEP 1B—A series of manually segmented DICOM+Volumetric mask datasets (only one of which is shown in this FIG. 6) are utilized to train the machine learning algorithm. The result of the process at this point (block 603) is the trained machine dataset (only one of which is shown in this FIG. 6) which will be utilized in STEP 2C below.

Still referring to FIG. 6 certain specific details of a process for automated segmentation according to this embodiment are as follows: Block 604—Similar to block 601, a DICOM dataset. This block 604 dataset can represent, for example, a patient (as opposed, for example, to the training subject of block 601). STEP 2A—DICOM dataset (block 604) is cropped to eliminate, e.g., non-cardiac region content. This results in a new cropped DICOM dataset (block 605). STEP 2B—The cropped DICOM dataset (block 605) is filtered to generate the new bias field corrected DICOM (block 606). STEP 2C—The bias field corrected DICOM dataset (block 606, which is shown again in this FIG. 6 in the bottom row for clarity) is compared to the previously trained machine dataset (block 603, which is shown again in this FIG. 6 in the bottom row for clarity) to generate at STEP 2D a new block 607, which is a DICOM dataset with a selected volumetric mask which corresponds to the desired anatomy.

Figure 7:
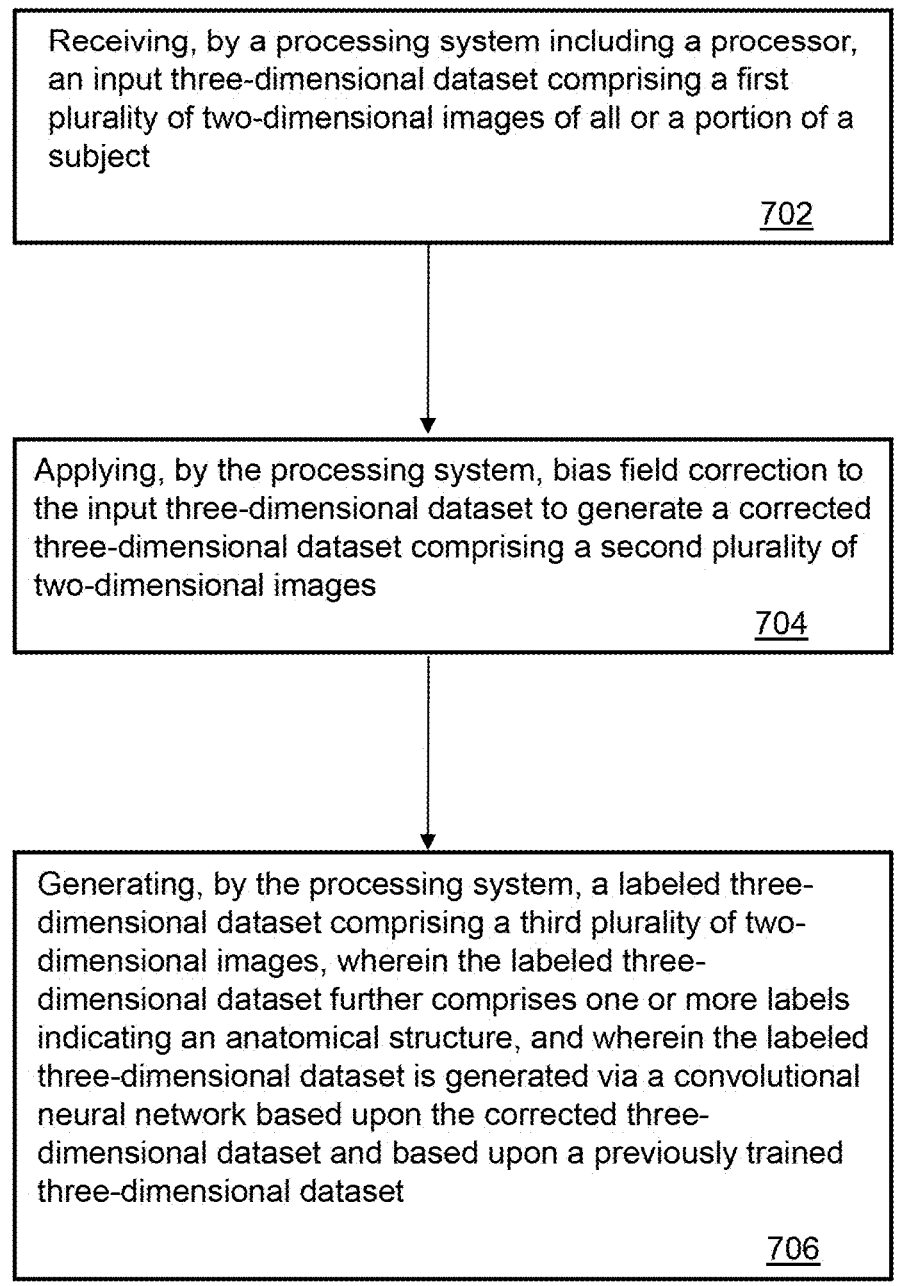
FIG. 7 depicts a method according to an embodiment.

Referring now to FIG. 7, various steps of a method 700 according to an embodiment are shown. As seen in this FIG. 7, step 702 comprises receiving, by a processing system including a processor, an input three-dimensional dataset comprising a first plurality of two-dimensional images of all or a portion of a subject. Next, step 704 comprises applying, by the processing system, bias field correction to the input three-dimensional dataset to generate a corrected three-dimensional dataset comprising a second plurality of two-dimensional images. Next, step 706 comprises generating, by the processing system, a labeled three-dimensional dataset comprising a third plurality of two-dimensional images, wherein the labeled three-dimensional dataset further comprises one or more labels indicating an anatomical structure, and wherein the labeled three-dimensional dataset is generated via a convolutional neural network based upon the corrected three-dimensional dataset and based upon a previously trained three-dimensional dataset.

Figure 8:
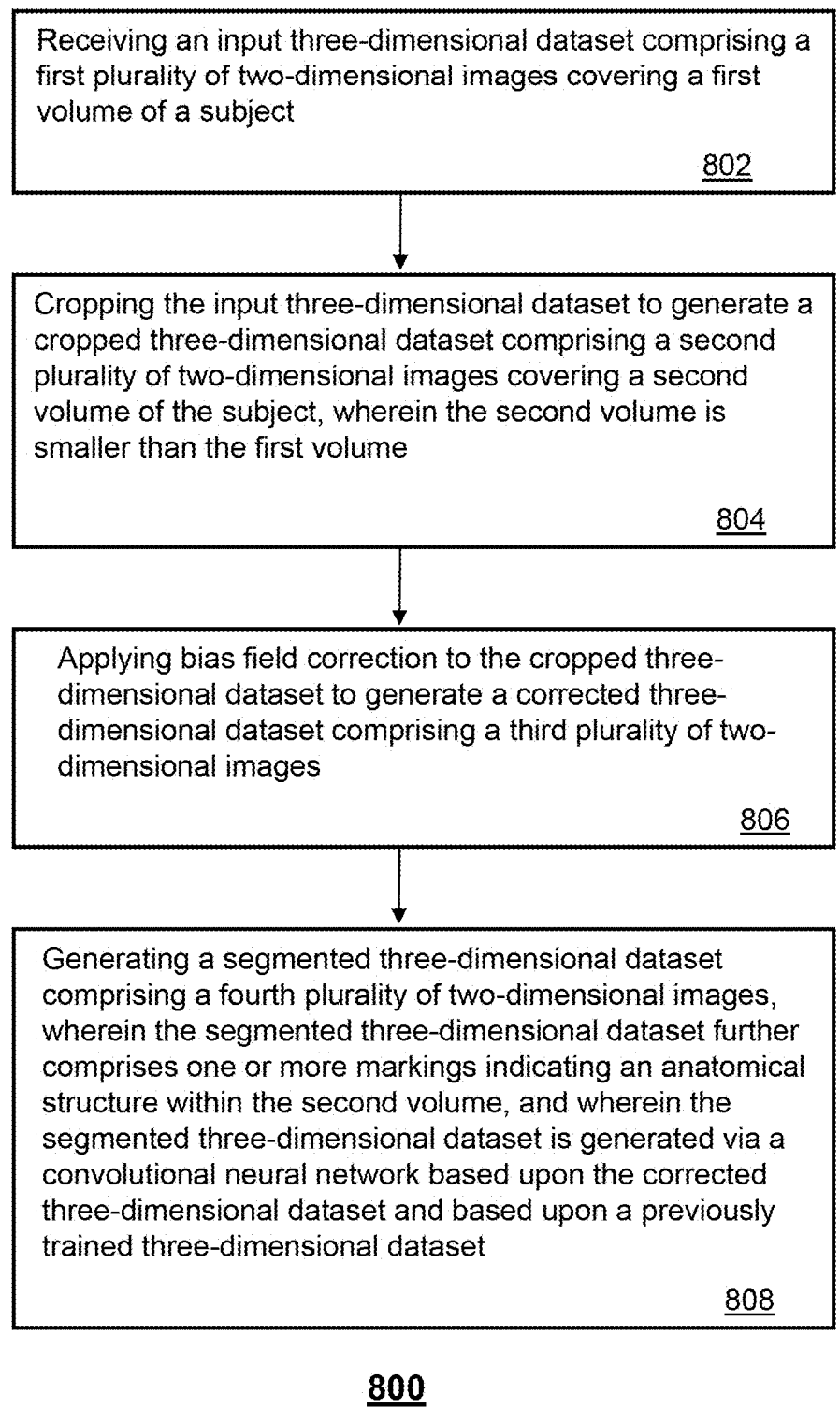
FIG. 8 depicts a method according to an embodiment.

Referring now to FIG. 8, various steps of a method 800 according to an embodiment are shown. As seen in this FIG. 8, step 802 comprises receiving an input three-dimensional dataset comprising a first plurality of two-dimensional images covering a first volume of a subject. Next, step 804 comprises cropping the input three-dimensional dataset to generate a cropped three-dimensional dataset comprising a second plurality of two-dimensional images covering a second volume of the subject, wherein the second volume is smaller than the first volume. Next, step 806 comprises applying bias field correction to the cropped three-dimensional dataset to generate a corrected three-dimensional dataset comprising a third plurality of two-dimensional images. Next, step 808 comprises generating a segmented three-dimensional dataset comprising a fourth plurality of two-dimensional images, wherein the segmented three-dimensional dataset further comprises one or more markings indicating an anatomical structure within the second volume, and wherein the segmented three-dimensional dataset is generated via a convolutional neural network based upon the corrected three-dimensional dataset and based upon a previously trained three-dimensional dataset.

Referring now to FIG. 9, various steps of a method 900 according to an embodiment are shown. As seen in this FIG. 9, step 902 comprises obtaining a trained three-dimensional dataset comprising a first plurality of two-dimensional images covering a first volume of a training subject, wherein the trained three-dimensional dataset is based upon one or more first magnetic resonance imaging scans of the training subject. Next, step 904 comprises obtaining an input three-dimensional dataset comprising a second plurality of two-dimensional images covering a second volume of a patient, wherein the input three-dimensional dataset is based upon one or more second magnetic resonance imaging scans of the patient. Next, step 906 comprises cropping the input three-dimensional dataset to generate a cropped three-dimensional dataset comprising a third plurality of two-dimensional images covering a third volume of the patient, wherein the third volume is smaller than the second volume. Next, step 908 comprises applying bias field correction to the cropped three-dimensional dataset to generate a corrected three-dimensional dataset comprising a fourth plurality of two-dimensional images. Next, step 910 comprises generating a segmented three-dimensional dataset comprising a fifth plurality of two-dimensional images, wherein the segmented three-dimensional dataset further comprises one or more markings indicating an anatomical structure within the third volume, and wherein the segmented three-dimensional dataset is generated via a convolutional neural network based upon the corrected three-dimensional dataset and based upon the trained three-dimensional dataset. In one specific example, the first volume is substantially the same as the third volume.

As described herein are mechanisms for providing 3D segmented organ models from raw MRI data (e.g., for use as a pre-surgical tool).

As described herein are mechanisms for providing a fully automated software pipeline to take raw MRI data and convert into a patient-specific 3D model (e.g., to be used for planning surgery). In one specific example, myocardium segmentation can be fully automated.

As described herein are mechanisms applicable to organ surgeries, which are tending to use more 3D virtual and physical models for planning (various embodiments described herein to generate 3D models can be more accurate than certain conventional methods to generate 3D models).

As described herein are mechanisms that provide higher fidelity 3D models of organs as compared to certain conventional methods (which can be of low fidelity and often misrepresent important physical aspects of the organs).

As described herein are mechanisms that provide an automated pipeline that is a plug-and-play tool to be used by hospital staff (e.g., support staff) to create accurate models. In one specific example, the tool can provide access (for non-experts) to model creation. Further, in this example, the tool can provide accurate representations that are necessary for experts.

As described herein are mechanisms that can be used in the context of surgical planning for cardiac procedures (often the heart is the most difficult organ to model because of movement).

As described herein are mechanisms that provide fully automated workflow to generate 3D digital heart models directly from MR scans (in one specific example, this workflow can be used by non-experts to create hi-fidelity models of the heart for surgical planning).

As described herein are mechanisms that address model fidelity, particularly for models of soft tissue.

As described herein are mechanisms that take a 3D whole heart cardiac MRI and automate the segmentation of the myocardial and vessel walls from the imaging sequence, thereby generating a 3D digital model of the target structure(s).

As described herein, various embodiments can be used in the context of myocardium segmentation, deep learning, heart models, 3D printing, pre-surgery planning, congenital heart disease, automated segmentation, virtual reality, image processing, visualization, virtual environments, simulation, printing, and/or automated segmentation.

As described herein are mechanisms that can correct for a non-ideal experimental condition, specifically the bias field. In one specific example, use of the bias field correction procedure described herein can improve the performance of a deep learning based method.

As described herein are mechanisms for automatically creating 3D models from cardiac patients in clinical care.

As described herein are mechanisms for getting a highly reliable automated segmentation directly from the MRI data.

As described herein are mechanisms automating the process of placing a patient in the scanner (e.g., MRI) and a 3D model being automatically generated as an output.

As described herein are mechanisms that can allow non-experts to create 3D models that are typically only achievable conventionally by manual input from experts.

As described herein are mechanisms that can provide fully automated workflow with these steps: (a) Localize target heart volume; (b) Use convolution networks and multiplicative intrinsic component optimization (MICO) to create bias field correction, using algorithm training of the processor; and/or (c) Create myocardium segmentation using learning dense volumetric segmentation from sparse annotation.

As described herein, a "learned machine" component can be combined with certain subject matter expertise to produce a unique library of 3D models.

As described herein, in one embodiment a process for producing 3D models can comprise the following high-level steps: Receive/Input (e.g., data such as patient MRI scan(s)); Index/Filter (the data that is received/input); Select (the data that is indexed/filtered); Output (e.g., one or more 2D images and/or one or more 3D models).

In another embodiment, certain software (e.g., an algorithm called FAST—see https://fsl.fmrib.ox.ac.uk/fsl/fslwiki/FAST) can be used. This software can do bias field correction and also image segmentation based on image intensity values and a hidden Markov random field model and an EM algorithm (an EM algorithm refers to an expectation-maximization algorithm; FAST (which is fMRIB's Automated Segmentation Tool) is often used for brain images). In certain testing of FAST on heart images, however, the muscle in the chest wall and the liver could not be adequately separated out from the heart tissue with the segmentation in the FAST software (such testing indicated that the bias field correction step might have been adequate).

In another embodiment the entire algorithm (or part of the algorithm) can be implemented in MATLAB as follows: (1) Registration of current heart image to the example subject in an applicable database using 'imregister' in MATLAB. (2) Use that transformation to take the mask that was defined on the example subject back into the space of the current heart (the heart can then be cropped). (3) Bias field correction using MICO (see, e.g., Chunming Li, John C. Gore, Christos Davatzikos. Multiplicative intrinsic component optimization (MICO) for MRI bias field estimation and tissue segmentation, Magn Reson Imaging 2014; 32: 913-923). MICO results in images with the bias field removed. These are bias field corrected images. (4) Apply the trained machine learning algorithm to do the segmentation—this is the algorithm that was trained on certain data with this process (these steps) applied to the training data. The U-Net structure is used for the machine learning and this is executed in the MATLAB interface to caffe: Matcaffe (training and application of the machine learning algorithm can be executed in MATLAB). The output of this is the segmented heart tissue—e.g., the stack of slices (images) with 1's where there is heart and 0's where there is other tissue: blood, other muscles, air spaces, bone, other tissues. (5) In MATLAB, take the stack of slices of 1's and 0's and extract the faces and surfaces of the 3D object using 'isosurface' in MATLAB. The result of this is the faces and vertices of a 3D object. Write the 3D object as, for example, an STL file—this is the 3D object that is printable and/or viewable in virtual reality.

As described herein, segmentation (such as for training purposes) can be performed by drawing (using an appropriate computer input device) directly on one or more DICOM files.

As described herein, various embodiments enable automated creation of soft tissue segmentations by in essence replicating a trained physician's knowledge. In one example, the automated creation of soft tissue segmentations can go beyond signal intensity to relational. In another example, the automated creation of soft tissue segmentations can go beyond signal intensity to the expected 3D form of human anatomy.

As described herein, 3D data can be collected, 2D images from the 3D data can be processed, and 3D data from the processed 2D images can be created.

As described herein, bias field correction can be utilized to remove shading across an image.

As described herein, bias field correction can be utilized to get uniform intensity across an object.

As described herein, the data used for training and the patient data can be identically (or similarly) cropped.

In various embodiments, segmentation and/or model creation can be applied to heart tissue, blood, muscle in chest wall, liver, and/or brain (e.g., brain tumors). In one specific example, the segmentation can be heart tissue vs everything else (that is, everything except heart tissue).

In various embodiments, any desired part or parts of the body (including the whole body) can be imaged and processed.

In various embodiments, the 2D images can be greyscale images. In one specific example, an expert manually segments greyscale images for training a machine learning algorithm and patient-specific greyscale images are segmented by the trained machine learning algorithm.

In various embodiments, an automated pipeline of the type described herein can reduce time required for the process (e.g., from around 2 hours for a conventional manual process to much less time). In one specific example, the process of an embodiment (post-training) can be implemented via automation such that the machine processing time (which, in this example, does not require manual user input after being initiated) is 5-15 minutes.

Figure 10:
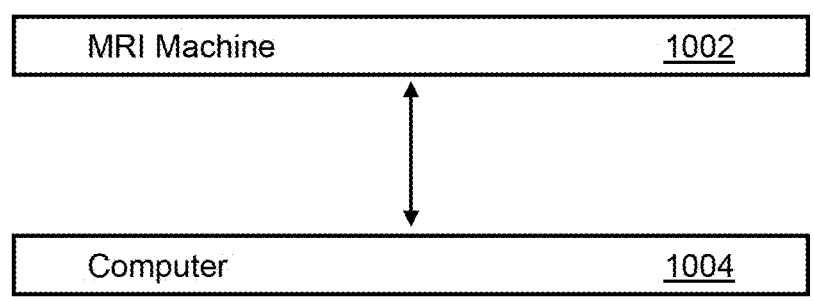
FIG. 10 depicts an illustrative diagrammatic representation of a system according to an embodiment.

In various embodiments, the orientation information in DICOM files can be utilized. In one specific example, the DICOM orientation information can be used to register image(s) after the fact. In another specific example, the 2D images can be put back into their original orientation. In another specific example, a default view can be re-oriented to a particular anatomy as acquired. In another specific example, an output can comprise one or more 3D models and/or one or more 2D images Referring now to FIG. 10, this depicts an illustrative diagrammatic representation of a system 1001 according to an embodiment. As seen in this FIG. 10, system 1001 includes MRI machine 1002 in operative communication with computer 1004. The MRI machine 1002 can obtain MRI data from a training subject (not shown) and/or a patient (not shown) and can be controlled by and/or provide data to the computer 1004. In one specific example, one or more pulse sequences (such as described herein) can be implemented in MRI machine 1002 and/or computer 1004 by software (and/or by software in combination with firmware/hardware). In one specific example, the MRI machine (which can be referred to as a scanner) comprises several elements: a magnet (usually a superconducting solenoidal magnet) that provides a static magnetic field, as well as gradient coils used to introduce time-varying and spatially-varying magnetic fields. Nuclear Magnetic Resonance active nuclei, such as $^1$H, located in the magnetic field of the main magnet, can be excited by the use of Radio Frequency (RF) transmitters in concert with resonant coils, such as a body coil. These excited nuclei are manipulated via magnetic field gradients induced by the gradient coils and associated hardware to encode imaging data in the nuclear magnetic resonance signals emitted by the object being imaged and sampled by RF receiver hardware in concert with resonant coils. The coordination of RF transmit pulses, magnetic field gradients, and RF receiver sampling are all coordinated by computer systems running a specific program that implements a scheme, called a pulse sequence, to image the object. Once the data is received from the object, using knowledge of the pulse sequence and the received data, the data is reconstructed using Fourier transforms, and other knowledge about the physics of the MR imaging process to generate human readable images. All of this is coordinated via a human interface, often known as a console or host, where users can visualize the results of scans, and prescribe additional scans, often inputting parameters into the pulse sequences to obtain specific types of images.

Figure 11:
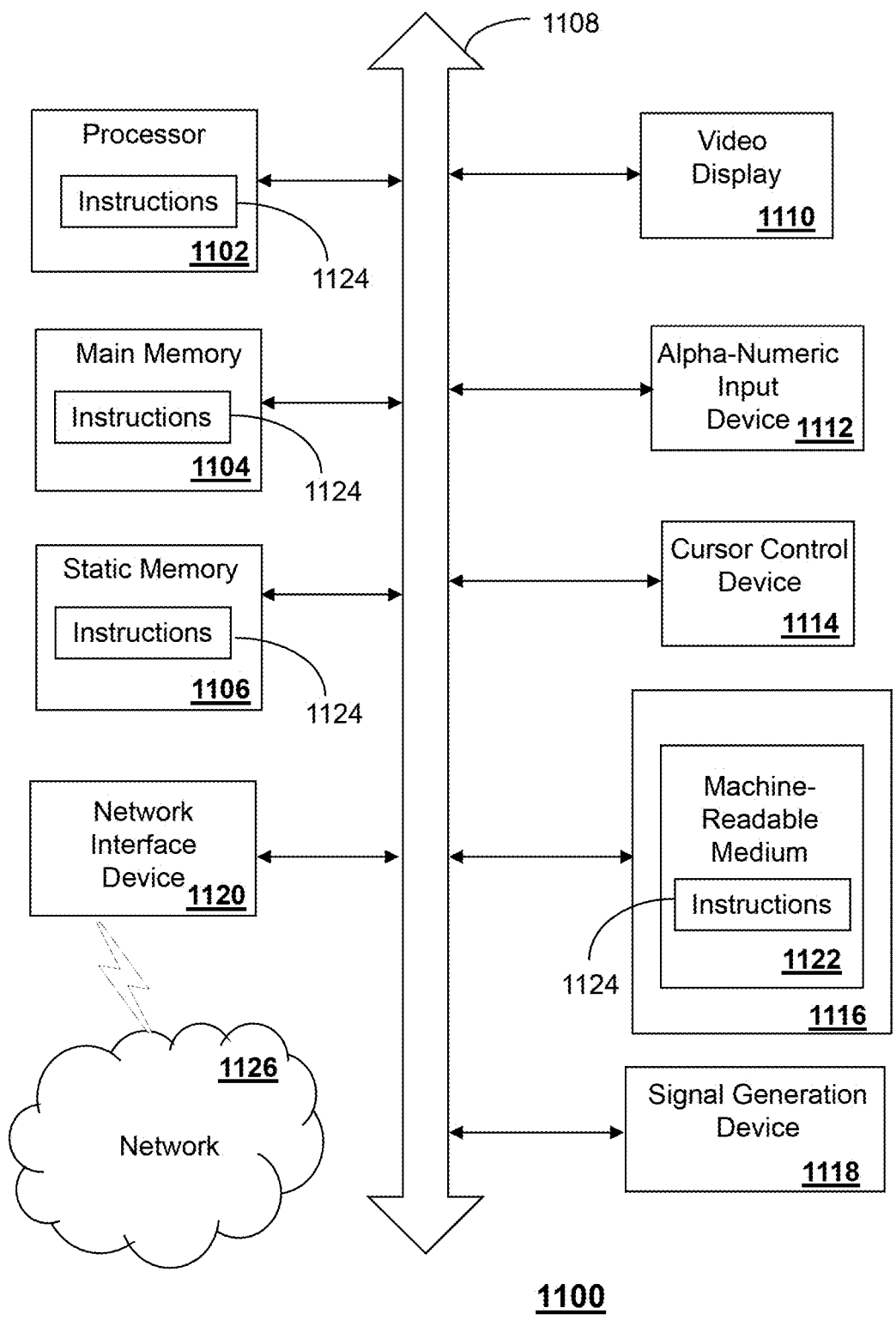
FIG. 11 depicts an embodiment showing an illustrative diagrammatic representation of a machine in the form of a computer system within which a set of instructions, when executed, may cause the machine to perform any one or more of the methodologies disclosed herein.

Referring now to FIG. 11, this depicts an illustrative diagrammatic representation of a machine in the form of a computer system 1100 within which a set of instructions, when executed, may cause the machine to perform any one or more of the methods discussed herein. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1100 may include a processor 1102 (e.g., a central processing unit (CPU), a graphics processing unit (GPU, or both), a main memory 1104 and a static memory 1106, which communicate with each other via a bus 1108. The computer system 1100 may further include a video display unit 1110 (e.g., a liquid crystal display (LCD), a flat panel, or a solid state display). The computer system 1100 may include an input device 1112 (e.g., a keyboard), a cursor control device 1114 (e.g., a mouse), a disk drive unit 1116, a signal generation device 1118 (e.g., a speaker or remote control) and a network interface device 1120.

The disk drive unit 1116 may include a tangible computer-readable storage medium 1122 on which is stored one or more sets of instructions (e.g., software 1124) embodying any one or more of the methods or functions described herein, including those methods illustrated above. The instructions 1124 may also reside, completely or at least partially, within the main memory 1104, the static memory 1106, and/or within the processor 1102 during execution thereof by the computer system 1100. The main memory 1104 and the processor 1102 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 1122 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1100.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method comprising:
   receiving, by a processing system including a processor, an input three-dimensional dataset comprising a first plurality of two-dimensional images, wherein the first plurality of two-dimensional images covers an entire myocardium of a subject, and wherein the input three-dimensional dataset had been generated based upon one or more magnetic resonance imaging scans of the subject;
   applying, by the processing system, bias field correction to the input three-dimensional dataset to generate a corrected three-dimensional dataset comprising a second plurality of two-dimensional images;
   generating, by the processing system, a labeled three-dimensional dataset comprising a third plurality of two-dimensional images, wherein the labeled three-dimensional dataset further comprises one or more labels associated with the entire myocardium of the subject, and wherein the labeled three-dimensional dataset is generated via a convolutional neural network based upon the corrected three-dimensional dataset and based upon a previously trained three-dimensional dataset; and
   outputting, by the processing system, a three-dimensional digital model of the entire myocardium of the subject based upon the labeled three-dimensional dataset;
   wherein the method operates in an automatic manner proceeding without manual user intervention after the receiving the input three-dimensional dataset to the applying the bias field correction and then to the generating the labeled three-dimensional dataset and then to the outputting the three-dimensional digital model.

2. The method of claim 1, wherein the one or more labels are part of the third plurality of two-dimensional images.

3. The method of claim 1, wherein the bias field correction comprises altering a plurality of signal intensity elements of the first plurality of two-dimensional images.

4. The method of claim 1, wherein the one or more labels are applied to the third plurality of two-dimensional images.

5. The method of claim 1, further comprising receiving, by the processing system, the previously trained three-dimensional dataset, wherein the previously trained three-dimensional dataset had been generated based upon images that had been manually segmented.

6. The method of claim 1, wherein the outputting comprises facilitating display of the three-dimensional digital model on a display screen.

7. A device comprising:
a processing system including a processor; and
a memory that stores executable instructions that, when executed by the processing system, perform operations, the operations comprising:
receiving an input three-dimensional dataset comprising a first plurality of two-dimensional images covering a first volume of a subject, wherein the first volume of the subject covers an entire myocardium of the subject, and wherein the input three-dimensional dataset had been generated based upon one or more magnetic resonance imaging scans of the subject;
cropping the input three-dimensional dataset to generate a cropped three-dimensional dataset comprising a second plurality of two-dimensional images covering a second volume of the subject, wherein the second volume of the subject is smaller than the first volume of the subject, and wherein the second volume of the subject comprises the entire myocardium of the subject;
applying bias field correction to the cropped three-dimensional dataset to generate a corrected three-dimensional dataset comprising a third plurality of two-dimensional images;
generating a segmented three-dimensional dataset comprising a fourth plurality of two-dimensional images, wherein the segmented three-dimensional dataset further comprises one or more markings associated with the entire myocardium of the subject within the second volume, and wherein the segmented three-dimensional dataset is generated via a convolutional neural network based upon the corrected three-dimensional dataset and based upon a previously trained three-dimensional dataset; and
outputting a three-dimensional digital model of the entire myocardium of the subject based upon the segmented three-dimensional dataset;
wherein the operations are performed in an automatic manner proceeding without manual user intervention after the receiving the input three-dimensional dataset to the cropping the input three-dimensional dataset and then to the applying the bias field correction and then to the generating the segmented three-dimensional dataset and then to the outputting the three-dimensional digital model.

8. The device of claim 7, wherein the one or more markings are part of the fourth plurality of two-dimensional images.

9. The device of claim 7, wherein the one or more markings are applied to the fourth plurality of two-dimensional images.

10. A machine-readable storage medium comprising executable instructions that, when executed by a processing system including a processor, facilitate performance of operations, the operations comprising:
obtaining:
a trained three-dimensional dataset comprising a first plurality of two-dimensional images covering a first volume of a training subject, wherein the trained three-dimensional dataset is based upon one or more first magnetic resonance imaging scans of the training subject; and
an input three-dimensional dataset comprising a second plurality of two-dimensional images covering a second volume of a patient, wherein the second volume of the patient covers an entire myocardium of the patient, and wherein the input three-dimensional dataset is based upon one or more second magnetic resonance imaging scans of the patient;
cropping the input three-dimensional dataset to generate a cropped three-dimensional dataset comprising a third plurality of two-dimensional images covering a third volume of the patient, wherein the third volume of the patient is smaller than the second volume of the patient, and wherein the third volume of the patient covers the entire myocardium of the patient;
applying bias field correction to the cropped three-dimensional dataset to generate a corrected three-dimensional dataset comprising a fourth plurality of two-dimensional images;
generating a segmented three-dimensional dataset comprising a fifth plurality of two-dimensional images, wherein the segmented three-dimensional dataset further comprises one or more markings associated with the entire myocardium of the patient within the third volume, and wherein the segmented three-dimensional dataset is generated via a convolutional neural network based upon the corrected three-dimensional dataset and based upon the trained three-dimensional dataset; and
outputting a three-dimensional digital model of the entire myocardium of the patient based upon the segmented three-dimensional dataset;
wherein the operations are performed in an automatic manner proceeding without manual user intervention after the obtaining the trained three-dimensional dataset and the input three-dimensional dataset to the cropping the input three-dimensional dataset and then to the applying the bias field correction and then to the generating the segmented three-dimensional dataset and then to the outputting the three-dimensional digital model.

11. The machine-readable storage medium of claim 10, wherein the trained three-dimensional dataset is further based upon one or more second magnetic resonance imaging scans of another training subject.

12. The machine-readable storage medium of claim 10, wherein the trained three-dimensional dataset had been generated based upon images that had been manually segmented.

13. The machine-readable storage medium of claim 10, wherein the bias field correction comprises altering a plurality of signal intensity elements of the third plurality of two-dimensional images.

14. The machine-readable storage medium of claim 10, wherein the outputting comprises facilitating display of the three-dimensional digital model on a display screen.

15. The machine-readable storage medium of claim 10, wherein the outputting comprises facilitating 3D printing, viewing in virtual reality, or any combination thereof.

16. The method of claim 1, wherein the outputting comprises facilitating 3D printing, viewing in virtual reality, or any combination thereof.

17. The device of claim 7, wherein the operations further comprise receiving the previously trained three-dimensional dataset.

18. The device of claim 17, wherein the previously trained three-dimensional dataset had been generated based upon images that had been manually segmented.

19. The device of claim 7, wherein the bias field correction comprises altering a plurality of signal intensity elements of the second plurality of two-dimensional images.

20. The device of claim 7, wherein the outputting comprises facilitating 3D printing, viewing in virtual reality, or any combination thereof.

* * * * *